(12) United States Patent
Nett et al.

(10) Patent No.: US 12,205,253 B2
(45) Date of Patent: Jan. 21, 2025

(54) SYSTEMS AND METHODS FOR ADAPTIVE BLENDING IN COMPUTED TOMOGRAPHY IMAGING

(71) Applicant: GE Precision Healthcare LLC, Waukesha, WI (US)

(72) Inventors: Brian Edward Nett, Wauwatosa, WI (US); Jed Douglas Pack, Glenville, NY (US); Zhye Yin, Niskayuna, NY (US); Jie Tang, Merion Station, PA (US)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/480,384

(22) Filed: Oct. 3, 2023

(65) Prior Publication Data

US 2024/0029207 A1 Jan. 25, 2024

Related U.S. Application Data

(62) Division of application No. 16/807,586, filed on Mar. 3, 2020, now Pat. No. 11,810,276.

(51) Int. Cl.
| | | |
|---|---|---|
| *G06T 5/50* | (2006.01) | |
| *A61B 6/00* | (2006.01) | |
| *A61B 6/02* | (2006.01) | |
| *G01N 23/046* | (2018.01) | |
| *G06T 5/20* | (2006.01) | |
| *G06T 5/70* | (2024.01) | |

(Continued)

(52) U.S. Cl.
CPC ............... *G06T 5/50* (2013.01); *A61B 6/027* (2013.01); *A61B 6/5229* (2013.01); *A61B 6/5258* (2013.01); *G01N 23/046* (2013.01); *G06T 5/20* (2013.01); *G06T 5/70* (2024.01); *G06T 11/006* (2013.01); *G06T 11/008* (2013.01); *A61B 6/032* (2013.01); *G01N 2223/401* (2013.01); *G06T 2207/10081* (2013.01); *G06T 2207/20084* (2013.01); *G06T 2207/20221* (2013.01); *G06T 2207/30004* (2013.01); *G06T 2210/41* (2013.01); *G06T 2211/421* (2013.01); *G06T 2211/424* (2013.01)

(58) Field of Classification Search
None
See application file for complete search history.

(56) References Cited

U.S. PATENT DOCUMENTS

2011/0280459 A1* 11/2011 Nakanishi ............... A61B 6/032
378/4
2012/0308100 A1 12/2012 Pack
(Continued)

OTHER PUBLICATIONS

Li et al., "Adaptive nonlocal means filtering based on local noise level for CT denoising," Medical Physics, vol. 41, No. 1, Jan. 2014, 16 pages.

*Primary Examiner* — Hoon K Song (57) ABSTRACT

Systems and methods are provided for computed tomography (CT) imaging. In one embodiment, a method comprises adaptively blending at least two input image volumes with different spatially-variant noise characteristics to generate an output image volume with uniform noise throughout the output image volume. In this way, images may be reconstructed from projection data with data redundancy without introducing image artifacts from stitching images or variance in image noise due to the data redundancy.

8 Claims, 7 Drawing Sheets

(51) Int. Cl.
    *G06T 11/00*     (2006.01)
    *A61B 6/03*     (2006.01)

(56) References Cited

U.S. PATENT DOCUMENTS

2016/0015350 A1   1/2016   Chang
2018/0300908 A1   10/2018   Zabic \* cited by examiner

SYSTEMS AND METHODS FOR ADAPTIVE BLENDING IN COMPUTED TOMOGRAPHY IMAGING

CROSS-REFERENCE TO RELATED APPLICATIONS

This application is a divisional of U.S. application Ser. No. 16/807,586, filed on Mar. 3, 2020, the disclosure of which is incorporated herein by reference in its entirety.

FIELD

Embodiments of the subject matter disclosed herein relate to non-invasive diagnostic imaging, and more particularly, to adaptive blending in computed tomography (CT) imaging.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

BRIEF DESCRIPTION

In one embodiment, a method comprises adaptively blending at least two input image volumes with different spatially-variant noise characteristics to generate an output image volume with uniform noise throughout the output image volume. In this way, images may be reconstructed from projection data with data redundancy without introducing image artifacts from stitching images or variance in image noise due to the data redundancy.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 6:
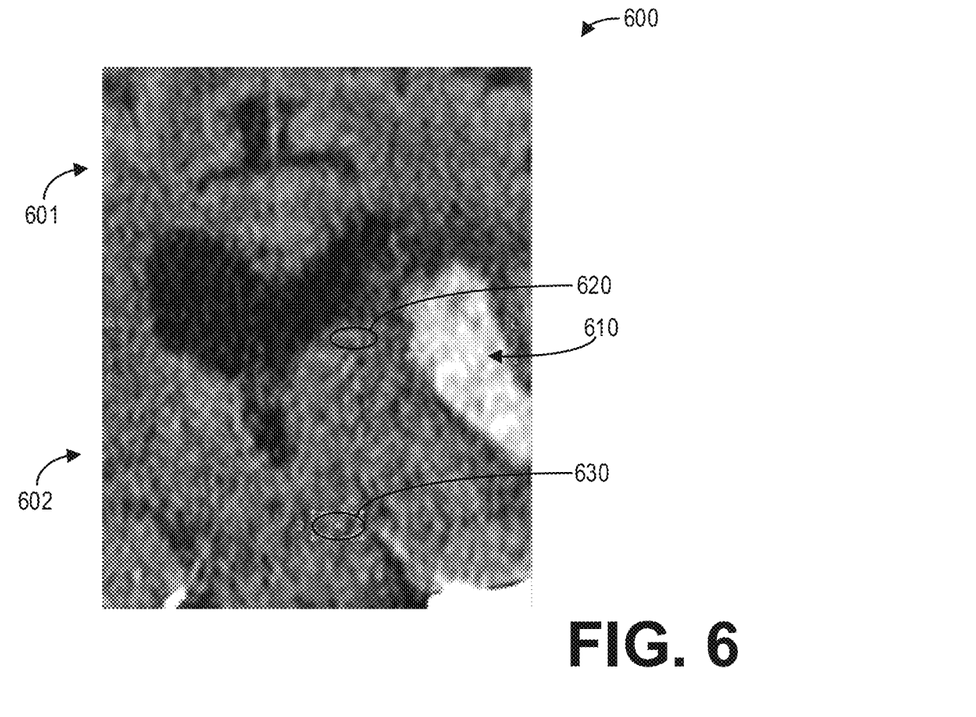
FIG. 6 shows an example output image generated from two image volumes without blending.
Figure 7:
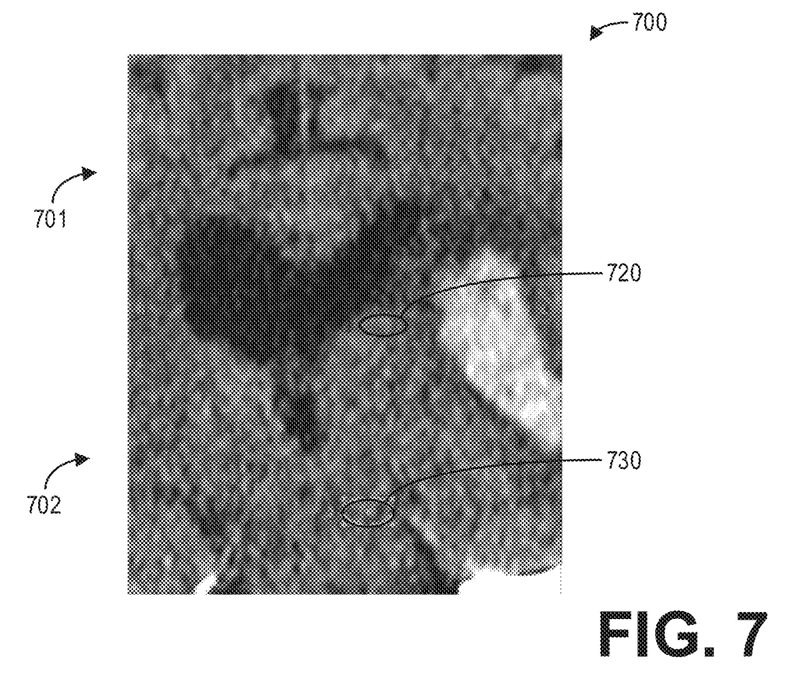
FIG. 7 shows an example output image generated from two image volumes with smooth blending.
Figure 8:
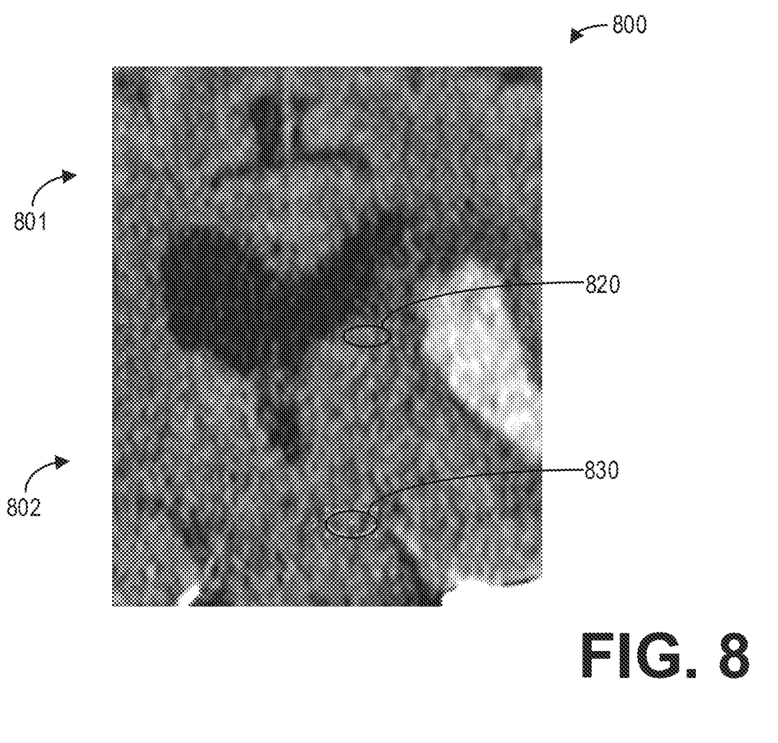
FIG. 8 shows an example output image generated from two image volumes with adaptive blending according to an embodiment.

The following description relates to various embodiments of medical imaging systems. In particular, systems and methods are provided for the adaptive blending of CT images to reconstruct an image of a target volume with uniform noise characteristics. An example of a CT imaging system that may be used to acquire images processed in accordance with the present techniques is provided in FIGS. 1 and 2. One approach to reconstructing images with uniform noise characteristics, such as the methods depicted in FIGS. 3-5, may include combining multiple images with spatially-varying noise characteristics into a noise-neutral blended image. FIGS. 6-8 shows three examples for combining image volumes, including an example wherein images are not blended, an example wherein images are blended but without attention to noise characteristics, and an example wherein images are adaptively blended to attain a uniform noise distribution over the combined images.

In both axial and helical scanning modes, there are conditions when a number of measurements may vary over an image volume. This may be referred to as data redundancy. Since the noise of an image reconstructed from CT projection data depends on the number of measurements, a change in the number of measurements used to reconstruct different spatial locations in the image may result in non-uniform noise properties in the image.

There are multiple image processing tools such as non-linear filters, iterative reconstruction, and deep learning models are available to reduce noise in CT images. However, most noise reduction methods may not completely account for variations in the data redundancy throughout an image volume. Thus, even with the use of existing image processing tools for reducing noise, data redundancy may still cause non-uniform noise properties throughout an image volume.

As an example, image volumes obtained from a CT scan may be blended to achieve uniform noise throughout the image volume. The output volume may be a weighted average of multiple input volumes having spatially variant noise characteristics. The image volume obtained after a CT scan of a subject may be processed using one or more of filter backprojection (FBP), convolutional neural network, and non-linear image filters. An actual image and a maximally denoised image from each image volume may be used to obtain a noise-adjusted volume. A prescribed blending ratio and a tuning parameter may be used to obtain the noise-adjusted volumes. In some examples, each image volume may be decomposed into a series of sector images each with a limited spatial frequency range prior to blending with their corresponding sector images from another image. Two images volumes may be blended slice by slice. After blending of two image volumes, a standard deviation of the blended image outside of a blending region and a standard deviation of the blended image inside of the blending region may be calculated. The standard deviation outside the blending region and the standard deviation inside the blending region may be equated to solve for an updated blending ratio. Locational blending weights may be computed as a function of relative location of an image slice with respect to the center of the blended image. Noise-adjusted blended image volumes may be computed as a function of the locational blending weights, the updated blending ratio, actual image, and a maximally denoised image for each image volume. Two or more noise-adjusted blended image volumes may be blended with respect to the locational blending weights to provide a noise-neutral blended image.

In this way, by adaptive blending of image volumes using locational blending, a uniform noise characteristics over a final image volume may be achieved. The technical effect of computing noise adjusted volumes based on relative location of image slices relative to the center of an overlap region, a prescribed blending ratio, and a tuning parameter is that data redundancy caused by variations in the number of measurements during a scan may be accounted for and a noise-neutral output image volume may be provided.

Though a CT imaging system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality.

Figure 1:
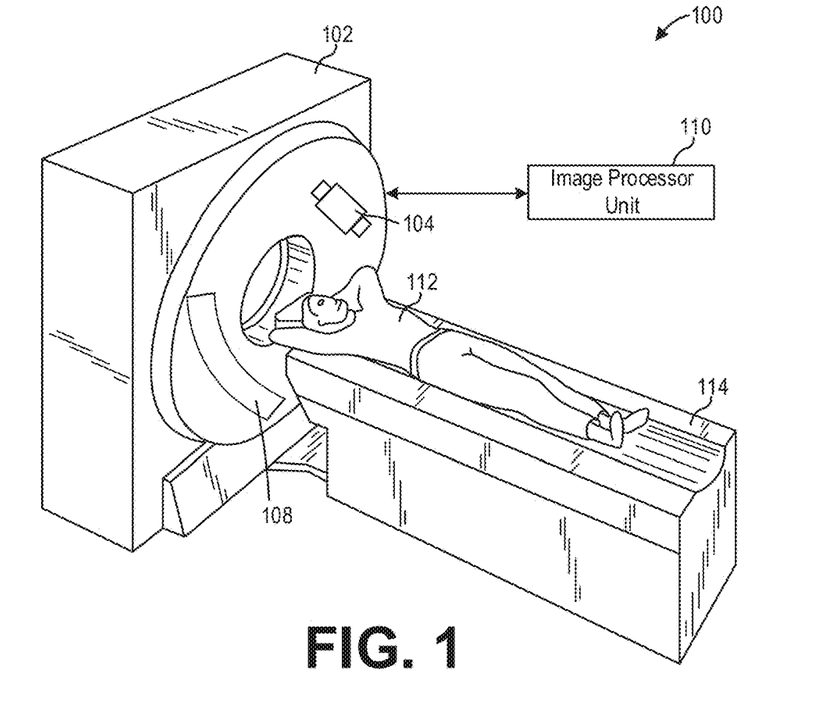
FIG. 1 shows a pictorial view of an imaging system according to an embodiment.

FIG. 1 illustrates an exemplary CT imaging system 100 configured for CT imaging. Particularly, the CT imaging system 100 is configured to image a subject 112 such as a patient, an inanimate object, one or more manufactured parts, and/or foreign objects such as dental implants, stents, and/or contrast agents present within the body. In one embodiment, the CT imaging system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts only a single x-ray source 104, in certain embodiments, multiple x-ray sources and detectors may be employed to project a plurality of x-ray radiation beams 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT imaging system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam attenuation at the detector location. The attenuation measurements from all the detector elements are acquired separately to produce a transmission profile.

In some CT imaging systems, the x-ray source and the detector array are rotated with a gantry within the imaging plane and around the object to be imaged such that an angle at which the radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

In an "axial" scan, a CT table with the patient positioned thereon may be moved to the desired location and then maintained stationary while the x-ray beam is rotated within the gantry, collecting data. A plurality of measurements from slices of a target volume may be reconstructed to form an image of the entire volume.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

Figure 2:
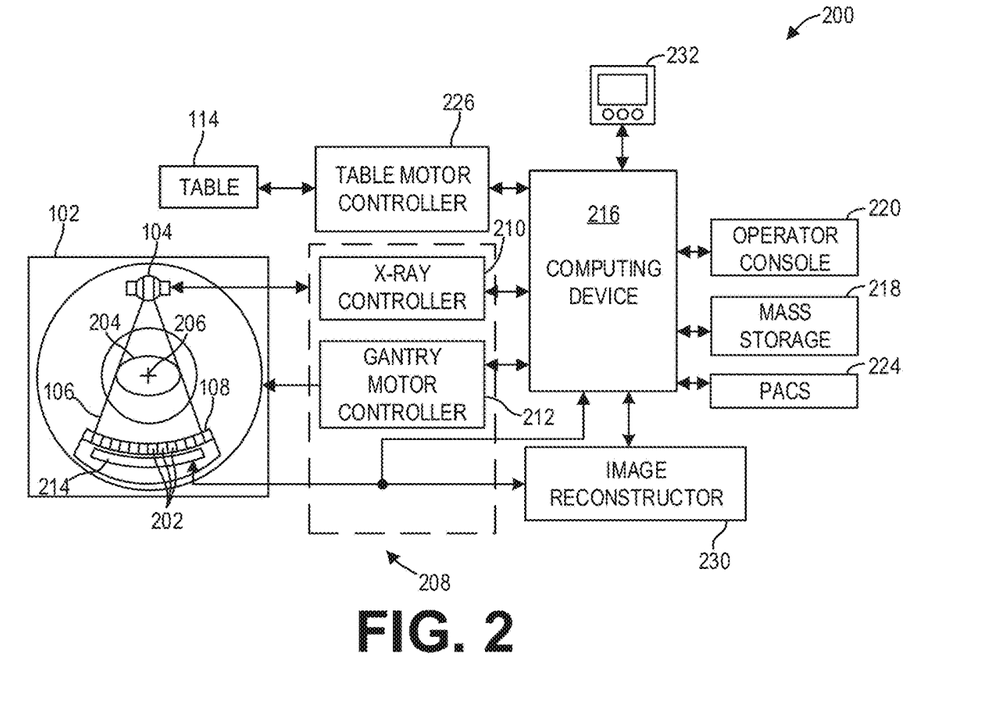
FIG. 2 shows a block schematic diagram of an exemplary imaging system according to an embodiment.

FIG. 2 illustrates an exemplary imaging system 200 similar to the CT imaging system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes (such as the methods described below with reference to FIGS. 3 and 4) described further herein may be stored as executable instructions in non-transitory memory on a computing device (or controller) in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

Figure 3:
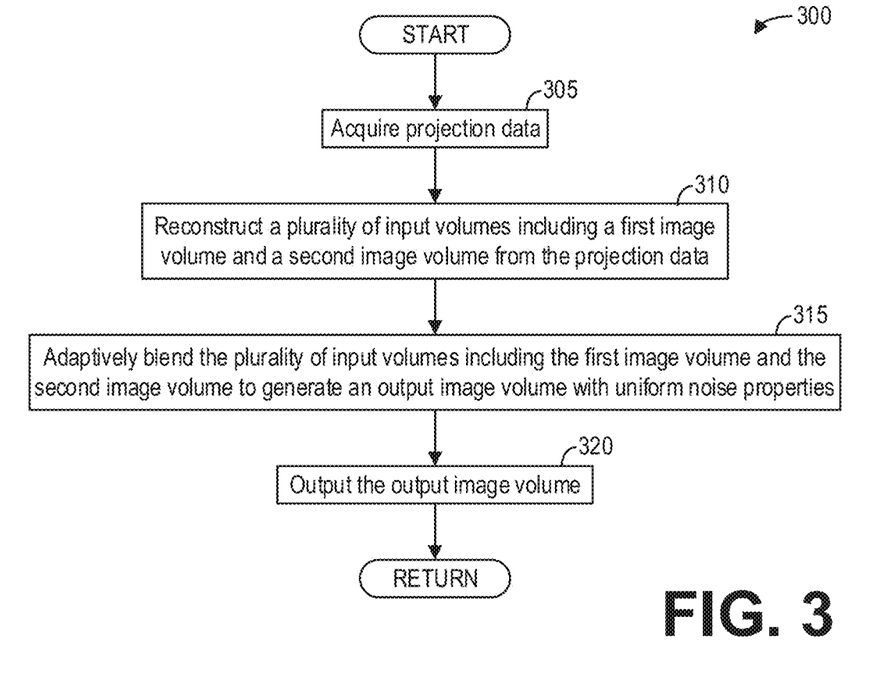
FIG. 3 shows a high-level flow chart illustrating an example method for adaptive blending in computed tomography imaging to achieve uniform noise according to an embodiment.

FIG. 3 shows a high-level flow chart illustrating an example method 300 for adaptive blending in computed tomography imaging to achieve uniform noise according to an embodiment. In particular, method 300 relates to adaptively blending image volumes with different spatially-variant noise characteristics to generate an output image volume with uniform noise throughout the image volume. Method 300 is described with regard to the systems and components of FIGS. 1 and 2, though it should be appreciated that the method 300 may be implemented with other systems and components without departing from the scope of the present disclosure. Method 300 may be implemented as executable instructions in non-transitory memory of one or more computing devices, such as the image reconstructor 230 and/or the computing device 216.

Method 300 begins at 305. At 305, method 300 acquires projection data. For example, method 300 may control the imaging system to scan a subject, such as a patient, in an axial mode or a helical mode. For example, for an axial mode, method 300 controls the imaging system to incrementally scan the subject and acquire a plurality of slices of projection data along the axial direction. That is, method 300 may control the gantry 102 to rotate the x-ray source 104 and the detector array 108 around the subject 204 at a first axial position, while also controlling the x-ray source 104 and the detector array 108 to acquire a first volume of projection data at the first axial position. The position of the table 114 with the subject 204 positioned thereon is then adjusted to a second axial position, and method 300 controls the gantry 102 to rotate the x-ray source 104 and the detector array 108 around the subject 204 at the second axial position, while also controlling the x-ray source 104 and the detector array 108 to acquire a second volume of projection data at the second axial position. Method 300 continues controlling the imaging system 200 in this way for a plurality of axial positions over a given distance in the axial direction, depending on the size of the region of interest being imaged. The volumes of projection data acquired at adjacent axial positions overlap so that the volumes may be combined to form a single image volume without loss of information. For example, the first volume of projection data at the first axial position and the second volume of projection data at the second axial position overlap by a predetermined amount.

For a helical mode, method 300 may control the table 114, via the table motor controller 226, to adjust the axial position of the subject 204 continuously while the gantry 102 rotates the x-ray source 104 and the detector array 108 about the subject 204. Meanwhile, method 300 controls the x-ray source 104 and the detector array 108 to acquire volumes of projection data as the gantry 102 is rotating and the table 114 is moving the subject 204 through the bore of the gantry 102 along the axial direction. Data redundancy in the projection data occurs when redundant projection data for a same view is acquired, and so the amount and location of data redundancy varies based on the starting table location, the starting view angle, the ending view angle, and the helical pitch (e.g., the speed of the table 114 and the rotation speed of the gantry 102).

Thus, during an axial mode, the x-ray source 104 and the detector array 108 move in a circular trajectory relative to the subject 204 at a plurality of axial positions to acquire projection data. In contrast, during a helical mode, the x-ray source 104 and the detector array 108 move in a helical trajectory relative to the subject to acquire the projection data. In both modes, there is data redundancy in the projection data acquired.

After acquiring the projection data at 305, method 300 continues to 310. At 310, method 300 reconstructs a plurality of input volumes including a first image volume and a second image volume from the projection data. For example, for an axial scan, method 300 may reconstruct the first image volume from the first volume of projection data and the second image volume from the second volume of projection data.

The plurality of input volumes may further include additional image volumes related to the first image volume and the second image volume but with different noise characteristics. For example, the plurality of input volumes may include the first image volume reconstructed from the first volume of projection data and an additional image volume also reconstructed from the first volume of projection data, but with different reconstruction techniques and/or noise reduction techniques applied to the reconstructed image volume, so that the noise characteristics of the first image volume and the additional image volume are different. For example, the first image volume may be reconstructed from the first volume of projection data with FBP, and additional noise-reduction methods such as non-linear image filters (e.g., non-local means, diffusion filters, edge-preserving filters, and so on) may be applied to the first image volume to generate the additional image volume. As another example, the first image volume may be reconstructed from the first volume of projection data with FBP, while the additional volume may be reconstructed from the first volume of projection data with a full volumetric iterative reconstruction algorithm including a forward and inverse model. As yet another example, the first image volume may be reconstructed from the first volume of projection data with FBP, while the additional image volume may be reconstructed from the first volume of projection data with a convolutional neural network to reduce the noise in the reconstructed image. As another example, the first image volume may be reconstructed from the first volume of projection data with FBP, while the additional image volume may be reconstructed from the first volume of projection data with FBP but configured with a different convolution kernel.

Method 300 applies the same approach used to reconstruct the first image volume and the additional image volume from the first volume of projection data to reconstruct the second image volume and another additional image volume from the second volume of projection data. In this way, the plurality of input volumes includes at least the first image volume, the second image volume, and two additional volumes reconstructed from the same volumes of projection data as the first and second image volumes, respectively, but with different noise characteristics. The plurality of input volumes may include an image volume for each volume of projection data acquired, as well as an additional corresponding image volume for each image volume as described hereinabove.

At 315, method 300 adaptively blends the plurality of input volumes including the first image volume and the second image volume to generate an output image volume with uniform noise properties. For example, method 300 adaptively blends the first image volume, the additional image volume corresponding to the first image volume with different noise characteristics, the second image volume, and the additional image volume corresponding to the second image volume with different noise characteristics to generate the output image volume. In particular, the output image volume is a weighted average of the plurality of input volumes, wherein the weights are designed or selected to achieve uniform noise throughout the output image volume. For example, the weights may be selected or determined based on the geometry of the imaging system. As another example, for helical scans, the weights may be selected or determined based on the starting table location, the starting view angle, the ending view angle, and the helical pitch. As another example, for an axial scan mode, the weights may be selected or determined based on the starting view angle for each volume of projection data, the ending view angle for each volume of projection data, and the overlap region between neighboring volumes of projection data.

In order to achieve a uniform noise throughout the output image volume, method 300 may further adjust the weights based on the noise levels of the individual input volumes. To that end, method 300 may compute a volumetric estimation of the image noise variation based on the attenuation of the raw projection data in addition to an analytic calculation. As another example, method 300 may compute a volumetric estimation of the image noise variation based on the attenuation of raw projection data, and the measured noise in the raw projection data in addition to the analytic calculation. As yet another example, method 300 may compute a volumetric estimation of the image noise variation based on an initial image reconstruction of an image volume from the projection data.

Thus, a weighting matrix may comprise the weights described hereinabove to account for the geometry of the imaging system during the scan, as well as the image noise variation as a function of spatial location in the input volumes. The input volumes may thus be adaptively blended according to the weights or blending weights of the weighting matrix. Further, in some examples, the blending weights may depend on spatial frequency in addition to spatial location. For example, each input volume may be decomposed into a series of sector images, each with a limited spatial frequency range, prior to being blended with their corresponding sector images from other corresponding input volumes.

At 320, method 300 outputs the output image volume. For example, the output image volume may be displayed via a display device, such as display 232. Additionally or alternatively, the output image volume may be stored in mass storage 218 for subsequent retrieval and display, and/or output to PACS 224 for remote storage and/or review. After outputting the output image volume, method 300 then returns.

Figure 4:
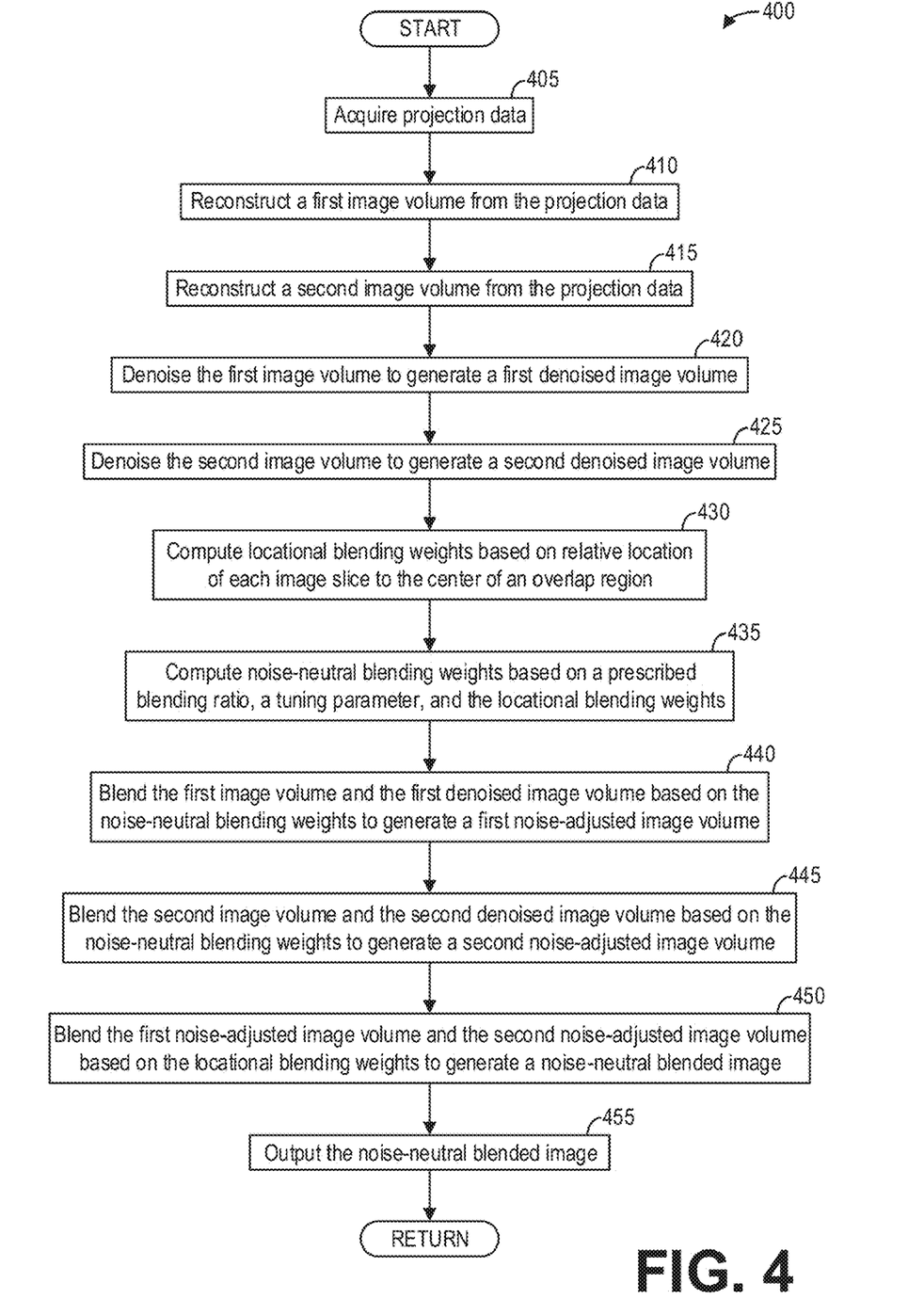
FIG. 4 shows a high-level flow chart illustrating an example method for noise-neutral blending of image volumes for axial acquisitions according to an embodiment.

FIG. 4 shows a high-level flow chart illustrating an example method 400 for noise-neutral blending of image volumes for axial acquisitions according to an embodiment. In particular, method 400 relates to combining measurements in a spatially variant manner to attain a noise-neutral image volume. Method 400 is described with regard to the systems and components of FIGS. 1 and 2, though it should be appreciated that the method 400 may be implemented with other systems and components without departing from the scope of the present disclosure. Method 400 may be implemented as executable instructions in non-transitory memory of one or more computing devices, such as the image reconstructor 230 and/or the computing device 216.

Method 400 begins at 405. At 405, method 400 acquires projection data during an axial scan of a subject, such as a patient. For example, method 400 controls the imaging system according to an axial mode to incrementally scan the subject and acquire a plurality of volumes of projection data along the axial direction. That is, method 400 may control the gantry 102 to rotate the x-ray source 104 and the detector array 108 around the subject 204 at a first axial position, while also controlling the x-ray source 104 and the detector array 108 to acquire a first volume of projection data at the first axial position. The position of the table 114 with the subject 204 positioned thereon is then adjusted to a second axial position, and method 400 controls the gantry 102 to rotate the x-ray source 104 and the detector array 108 around the subject 204 at the second axial position, while also controlling the x-ray source 104 and the detector array 108 to acquire a second volume of projection data at the second axial position. Method 400 continues controlling the imaging system 200 in this way for a plurality of axial positions over a given distance in the axial direction, depending on the size of the region of interest being imaged. The volumes of projection data acquired at adjacent axial positions overlap so that the volumes may be combined to form a single image volume without loss of information. For example, the first volume of projection data at the first axial position and the second volume of projection data at the second axial position overlap by a predetermined amount.

After acquiring the projection data, method 400 continues to 410. At 410, method 400 reconstructs a first image volume from the projection data. As an example, method 400 may reconstruct the first image volume with an analytic reconstruction algorithm such as a filter backprojection (FBP) technique. Alternatively, the first image volume may be reconstructed with an iterative reconstruction algorithm such as ASIR, CG, MLEM, MBIR, or another iterative reconstruction technique. As another example, the first image volume may be reconstructed with a machine-learning-based algorithm such as a convolutional neural network. Method 400 may reconstruct the first image volume from the first volume of projection data acquired at 405, as an illustrative example.

Further, at 415, method 400 reconstructs a second image volume from the image data. Method 400 may reconstruct the second image volume with the same image reconstruction technique used to reconstruct the first image volume. However, method 400 reconstructs the second image volume from a different volume of projection data, such as the second volume of projection data acquired at 405, than the first image volume. The first image volume and the second image volume at least partially overlap.

Continuing at 420, method 400 denoises the first image volume to generate a first denoised image volume. To denoise the first image volume, method 400 may process the first image volume with one or more noise-reduction methods such as a non-linear image filter (e.g., non-local means, diffusion filters, edge-preserving filters, and so on), as one example. As another example, method 400 may input the first image volume to a convolutional neural network trained to reduce image noise in the first image volume, thus producing the first denoised image volume. As another example, method 400 may iteratively reconstruct the first volume of projection data using a full volumetric iterative reconstruction algorithm containing a forward model and an inverse model to produce the first denoised image volume. As yet another example, method 400 may reconstruct the first volume of projection data into the first denoised image volume using FBP but with a different convolution kernel than was used to reconstruct the first image volume.

Similarly, at 425, method 400 denoises the second image volume to generate a second denoised image volume. To denoise the second image volume, method 400 may process the second image volume with one or more noise-reduction methods such as a non-linear image filter (e.g., non-local means, diffusion filters, edge-preserving filters, and so on), as one example. As another example, method 400 may input the second image volume to a convolutional neural network trained to reduce image noise in the second image volume, thus producing the second denoised image volume. As another example, method 400 may iteratively reconstruct the second volume of projection data using a full volumetric iterative reconstruction algorithm containing a forward model and an inverse model to produce the second denoised image volume. As yet another example, method 400 may reconstruct the second volume of projection data into the second denoised image volume using FBP but with a different convolution kernel than was used to reconstruct the second image volume. Method 400 may use the same denoising technique to produce both the first and second denoised image volumes.

At 430, method 400 computes locational blending weights based on a relative location of each image slice or image volume to the center of an overlap region, wherein the overlap region comprises the region of the first and second image volumes that overlap. The locational blending weights are computed or determined such that each image volume contributes 100% for each pixel or voxel outside of the overlap region, and furthermore such that contributions from each pixel or voxel of the image volumes decreases from the boundaries of the overlap region to the center of the overlap region. As a simple example, the contribution from the image volumes may range from 100% at the boundary of the overlap region to 50% at the center of the overlap region, with the contribution decreasing linearly from 100% at the boundary to 50% at the center of the overlap region, so that at the center of the overlap region both the first and second image volumes contribute 50%. Method 400 may further compute the locational blending weights based on the geometry of the imaging system during the scan, such that data redundancy in the overlap region is considered and adjusted for by the weights. For example, the weights may be adjusted so that the image volumes contribute differently according to the starting view angle and ending view angle for each image volume. Further, the weights may depend on spatial frequency in addition to or as an alternative to spatial position. For example, each image volume may be decomposed into a series of sector images with a limited spatial frequency range, which may then be blended with corresponding sector images, and the blending weights may be computed accordingly.

At 435, method 400 computes noise-neutral blending weights based on a prescribed blending ratio, a tuning parameter, and the locational blending weights. The prescribed blending ratio comprises a blending ratio of the image volumes with the corresponding denoised image volumes, and may be prescribed or adjusted according to determine the contributions from the denoising-free image volumes and the denoised image volumes. For a given image volume $V_0$ and a corresponding denoised image volume $V_D$, the blended image volume $V_{outside}$ outside of the overlap region or blending region is:

$$V_{outside} = m^*V_D + (1-m)^*V_0,$$

where m is the prescribed blending ratio. Accordingly, the noise level in terms of standard deviation $STD_{outside}$ for the blended image volume $V_{outside}$ outside of the overlap region is:

$$STD_{outside} = \sqrt{(m^*\sigma_D)^2 + ((1-m)^*\sigma_0)^2},$$

where $\sigma_D$ is the standard deviation of the denoised image volume $V_D$ and $\sigma_0$ is the standard deviation of the image volume $V_0$. Within the overlap region where the image volumes are blended, the overlap volume $V_{inside}$ is:

$$V_{inside} = w_1^*img_1 + w_2^*img_2,$$

where $w_1$ and $w_2$ are the locational blending weights, $img_1$ is the first blended image obtained from blending the first image volume $V_{0,1}$ with the first denoised image volume $V_{D,1}$, and $img_2$ is the second blended image obtained from blending the second image volume $V_{0,2}$ with the second denoised image volume $V_{D,2}$. Given the expression for the overlap volume $V_{inside}$, the image noise level in terms of standard deviation $STD_{inside}$ inside the overlap region is:

$$STD_{inside} = \sqrt{(w_1 * \sigma_{img1})^2 + (w_2 * \sigma_{img2})^2}.$$

To compute noise-neutral blending weights $m_{new}$ for blending the image volumes with the corresponding denoised image volumes, the first blended image $img_1$ may be expressed as:

$$img_1 = m_{new} * V_{D,1} + (1 - m_{new}) * V_{0,1},$$

where $m_{new}$ are the noise-neutral blending weights, $V_{D,1}$ is the first denoised image volume, and $V_{0,1}$ is the first image volume. Similarly, the second blended image $img_2$ is:

$$img_2 = m_{new} * V_{D,2} + (1 - m_{new}) * V_{0,2},$$

where $V_{D,2}$ is the second denoised image volume and $V_{0,2}$ is the second image volume. The standard deviation $\sigma_{img1}$ for the first blended image $img_1$ is therefore:

$$\sigma_{img1} = \sqrt{(m_{new} * \sigma_{D,1})^2 + ((1 - m_{new}) * \sigma_{0,1})^2},$$

while the standard deviation $\sigma_{img2}$ for the second blended image $img_2$ is:

$$\sigma_{img2} = \sqrt{(m_{new} * \sigma_{D,2})^2 + ((1 - m_{new}) * \sigma_{0,2})^2}.$$

Given the above, method 400 may calculate the noise-neutral blending weights $m_{new}$ by equating the noise estimation outside the overlap region to the noise estimation inside the overlap region, and solving for the noise-neutral blending weights $m_{new}$:

$$STD_{outside} = STD_{inside},$$

with the expressions for the noise estimation inside and outside the overlap region provided hereinabove.

In some examples, to simplify, method 400 may assume, for all images, that:

$$\sigma_0 = f * \sigma_D,$$

where f is the tuning parameter, such that the standard deviation of the denoised image volumes is the same:

$$\sigma_{D,1} = \sigma_{D,2}$$

and furthermore, so that the standard deviation of the denoising-free image volumes is the same:

$$\sigma_{0,1} = \sigma_{0,2}.$$

Since the image volumes are generally acquired with similar acquisition protocols and the image denoising is tuned to achieve similar noise reduction over similar acquisitions, these assumptions above are reasonable. Further, though f is expressed as a scaling parameter between the noise for the denoising-free image volumes and the denoised image volumes, as mentioned hereinabove the tuning parameter f may be tuned to improve the noise neutrality of the output image volume.

Thus, based on the prescribed blending ratio m, the tuning parameter f, and the locational blending weights ($w_1$, $w_2$), method 400 computes the noise-neutral blending weights $m_{new}$ that the image noise within the overlap region is similar or equal to the image noise outside of the overlap region, as described further herein.

After computing the noise-neutral blending weights, method 400 continues to 440. At 440, method 400 blends the first image volume and the first denoised image volume based on the noise-neutral blending weights to generate a first noise-adjusted image volume. For example, method 400 blends the first image volume $V_{0,1}$ with the first denoised image volume $V_{D,1}$ to generate the first noise-adjusted image volume $img_1$:

$$img_1 = m_{new} * V_{D,1} + (1 - m_{new}) * V_{0,1}.$$

Similarly, at 445, method 400 blends the second image volume and the second denoised image volume based on the noise-neutral blending weights to generate a second noise-adjusted image volume. For example, method 400 blends the second image volume $V_{0,2}$ with the second denoised image volume $V_{D,2}$ to generate the second noise-adjusted image volume $img_2$:

$$img_2 = m_{new} * V_{D,2} + (1 - m_{new}) * V_{0,2}.$$

At 450, method 400 blends the first noise-adjusted image volume and the second noise-adjusted image volume based on the locational blending weights to generate a noise-neutral blended image. For example, method 400 blends the first noise-adjusted image volume $img_1$ with the second noise-adjusted image volume $img_2$ according to the locational blending weights ($w_1$, $w_2$) to generate the noise-neutral blended image $V_{output}$:

$$V_{output} = w_1 * img_1 + w_2 * img_2.$$

At 455, method 400 outputs the noise-neutral blended image. For example, method 400 outputs the noise-neutral blended image $V_{output}$ to one or more of a display such as display 232, a storage device such as mass storage 218, or a PACS such as PACS 224. Method 400 then returns.

While the method 300 and the method 400 are described hereinabove as being performed via an imaging system such as the CT imaging system 100 or the imaging system 200, it should be appreciated that in some examples, the methods 300 and 400 may be implemented in other computing systems, such as a viewing workstation or a PACS such as PACS 224. In such examples, acquiring the projection data at 305 or 405 may comprise retrieving the projection data from non-transitory memory. Thus, the blending of the images may be accomplished on an imaging system such as the CT imaging system 100 or the imaging system 200, on a viewing workstation separate from an imaging system, or a PACS.

Figure 5:
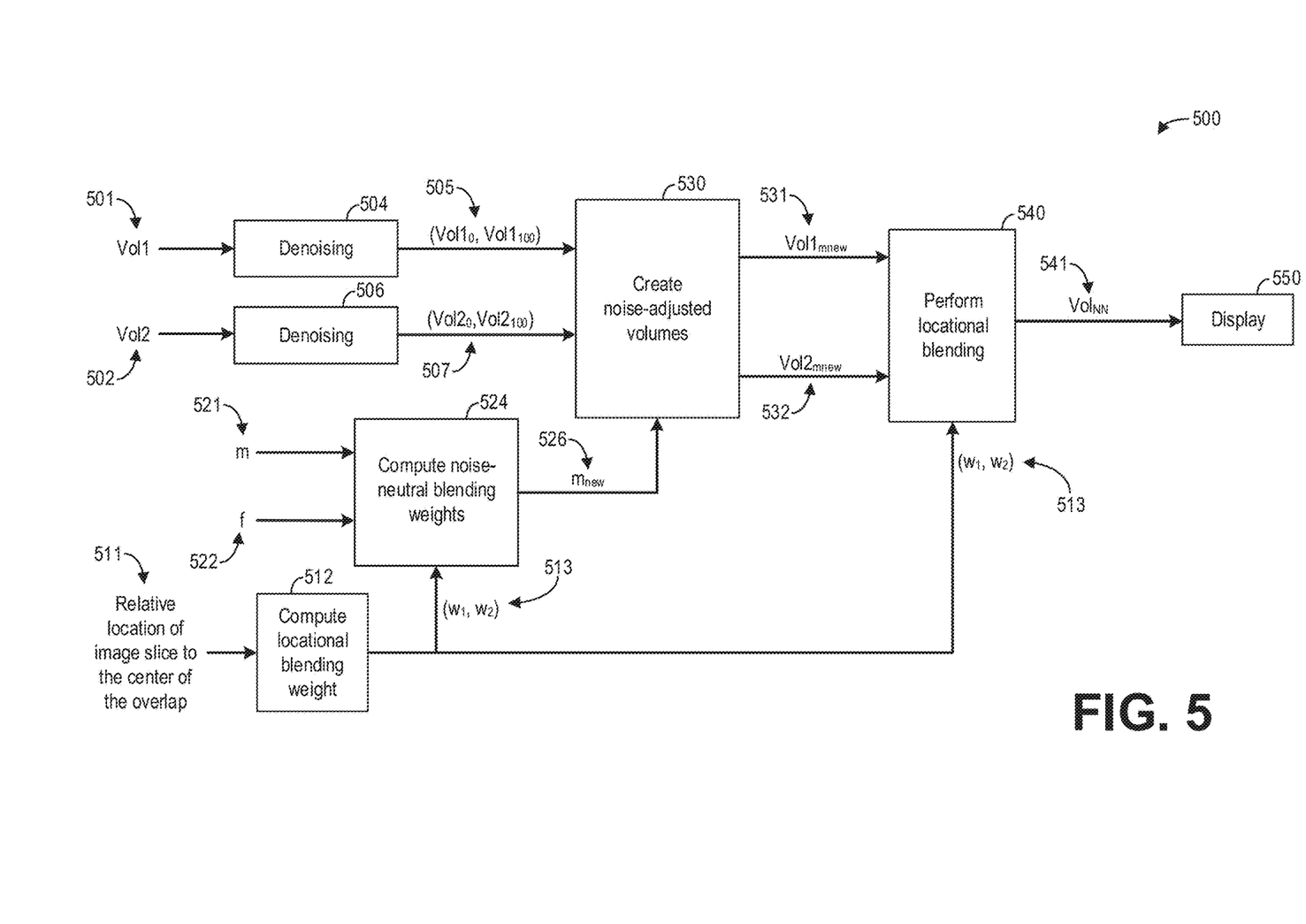
FIG. 5 shows a block diagram illustrating data components for noise-neutral blending of image volumes according to an embodiment.

As an illustrative and non-limiting example of an embodiment of the methods 300 and 400 described hereinabove, FIG. 5 shows a block diagram illustrating an example data flow 500 for the noise-neutral blending of image volumes according to an embodiment. A first image volume (Vol1) 501 and a second image volume (Vol2) 502 are reconstructed from projection data acquired during an axial scan, for example, such that the first image volume 501 and the second image volume 502 at least partially overlap.

Denoising 504 is applied to the first image volume 501 to produce a first denoised image volume $Vol1_{100}$. Denoising 504 comprises any suitable noise reduction technique for reducing the image noise in the first image volume 501, for example, or in some examples may comprise a different reconstruction from the same projection data as the first image volume 501 but with improved noise performance (e.g., through iterative reconstruction, FBP with a different reconstruction kernel, a convolutional neural network, and so on). The output of the denoising 504 thus comprises a set of input volumes 505 including a denoising-free image volume $Vol1_0$ comprising the original first image volume 501, where the subscript 0 indicates that zero (e.g., 0%) denoising has been applied to the image volume, as well as the first denoised image volume $Vol1_{100}$, where the subscript 100 indicates that maximum (e.g., 100%) denoising has been applied to the image volume. Denoising 506 is similarly applied to the second image volume 502 to produce a second denoised image volume $Vol2_{100}$. The output of the denoising 506 thus comprises a set of input volumes including a denoising-free image volume $Vol2_0$ comprising the original second image volume 502, as well as the denoised image volume $Vol2_{100}$.

In addition to the input volumes 505 and the input volumes 507, additional inputs for the data flow 500 include a relative location of each image slice (i.e., the image volumes 501 and 502) to the center of the overlap between the image slices or image volumes 501 and 502, a prescribed blending ratio (m) 521, and a tuning parameter (f) 522. The data flow 500 includes computing locational blending weights at 512 based on the relative location 511 of the image volumes to the center of the overlap.

The data flow 500 further includes computing noise-neutral blending weights at 524 based on the locational blending weights ($w_1$, $w_2$) 513 output from 512, the prescribed blending ratio 521, and the tuning parameter 522. The noise-neutral blending weights ($m_{new}$) 526 output from 524 are then input to 530 along with the input volumes 505 and 507, whereupon the data flow 500 includes creating noise-adjusted volumes. In particular, at 530, the input volumes 505 are blended according to the noise-neutral blending weights 526 to generate a first blended image volume ($Vol1_{mnew}$) 531, and the input volumes 507 are blended according to the noise-neutral blending weights 526 to generate a second blended image volume ($Vol2_{mnew}$) 532.

At 540, the data flow 500 includes performing locational blending of the first blended image volume 531 and the second blended image volume 532 according to the locational blending weights 513 to generate a noise-neutral image volume ($Vol_{NN}$) 541. The noise-neutral image volume 541 is output to a display 550, for example, or alternatively may be output to one or more of non-transitory storage such as mass storage 218 or a PACS such as PACS 224.

To illustrate how image volumes may be adaptively blended as discussed hereinabove to produce noise-neutral image volumes, FIGS. 6-8 depict different example output images comprising blended image volumes. In particular, FIG. 6 shows an example output image 600 generated from two image volumes without blending. That is, a first image volume 601 and a second image volume 602 are combined to form the output image 600, wherein each image volume 601 and 602 are formed from a combination of an image volume reconstructed via FBP and an image volume reconstructed via deep learning image reconstruction. However, without blending, a distinct linear image artifact 610 appears at the boundary between the image volumes 601 and 602. Further, an estimation of the noise within a first region-of-interest (ROI) 620 in the overlap region is 5.7 HU, whereas an estimation of the noise within a second ROI 630 in the center of the axial image volume 602, away from the overlap region, is 5.8 HU. Thus the noise level is similar, but the image artifact 610 is undesirable.

Meanwhile, FIG. 7 shows an example output image 700 generated from two image volumes with smooth blending. In particular, the output image 700 is formed from a first image volume 701 and a second image volume 702, formed from the same projection data as the image volumes 601 and 602, respectively. However, the image volumes 701 and 702 are blended linearly such that the contributions are equal (e.g., 50%) at the midpoint or center of the overlap region and tapers linearly to 0% at the border of the overlap. Since the data in the middle of the overlap region is equally weighted, there is a significant reduction in image noise. Specifically, an estimation of the noise within the first ROI 720 in the overlap region is 4.9 HU, while the estimation of the noise within the second ROI 730 in the center of the axial image volume 702 is still 5.8 HU. That is, while the image artifact 610 is eliminated in the output image 700 due to the linear or smooth blending of the image volumes 701 and 702, the noise distribution in the output image 700 is non-uniform through the overlap region.

FIG. 8 shows an example output image 800 generated from two image volumes with adaptive blending according to an embodiment. The output image 800 is formed by adaptively blending a first image volume 801 with a second image volume 802, formed from the same projection data as the image volumes 601 and 602, respectively. The image volumes 801 and 802 are blended as described hereinabove with regard to FIGS. 4 and 5. In particular, for each image volume 801 and 802, a higher contribution is given to the FBP reconstruction than the deep learning reconstruction in the overlap region when blending the FBP reconstruction and the deep learning reconstruction to form the image volumes 801 and 802. As a result, after blending the image volumes 801 and 802 with smooth locational blending weights, an estimation of the image noise in the first ROI 820 within the overlap region is 5.8 HU, while an estimation of the image noise in the second ROI 830 outside the overlap region is also 5.8 HU. Thus, by adaptively blending the image volumes, the image noise is uniform throughout the output image 800, while also eliminating image artifacts such as the image artifact 610.

A technical effect of the disclosure includes the generation of an image volume with uniform noise from a plurality of input image volumes with differing noise characteristics. Another technical effect of the disclosure includes the reduction of image artifacts from blending images acquired during an axial scan. Yet another technical effect of the disclosure includes blending of a plurality of images with different noise characteristics acquired during a scan into an image with uniform noise, wherein the plurality of images at least partially overlap, and wherein image noise within the overlapping region is equal to image noise outside of the overlapping region. The blending may cause the image noise within the overlapping to increase relative to the image noise of one or more of the plurality of images. Another technical effect of the disclosure includes the display of an image with uniform noise throughout the image.

In one embodiment, a method comprises adaptively blending at least two input image volumes with different spatially-variant noise characteristics to generate an output image volume with uniform noise throughout the output image volume.

In a first example of the method, the method further comprises reconstructing a first image volume and a second image volume from a first set of projection data, wherein image noise of the second image volume is reduced relative to image noise of the first image volume, and wherein the at least two input image volumes comprises the first image volume and the second image volume. In a second example of the method optionally including the first example, the method further comprises reconstructing a third image volume and a fourth image volume from a second set of projection data, wherein image noise of the fourth image volume is reduced relative to image noise of the third image volume, and wherein the at least two input image volumes further comprise the third image volume and the fourth image volume. In a third example of the method optionally including one or more of the first and second examples, the first image volume and the second image volume at least partially overlap the third image volume and the fourth image volume at an overlap region, and wherein image noise in the overlap region in the output image volume is equal to image noise away from the overlap region in the output image volume. In a fourth example of the method optionally including one or more of the first through third examples, the method further comprises reconstructing the first image volume via filtered backprojection, and processing the second image volume with one or more noise-reduction methods to reduce the image noise of the second image volume. In a fifth example of the method optionally including one or more of the first through fourth examples, the method further comprises reconstructing the first image volume via filtered backprojection, and reconstructing the second image volume via one of an iterative reconstruction algorithm, a convolutional neural network trained to reconstruct the second image volume with reduced noise, or filtered backprojection with a different convolution kernel. In a sixth example of the method optionally including one or more of the first through fifth examples, adaptively blending the at least two input image volumes comprises calculating weights for blending the at least two input image volumes, and combining the at least two input image volumes weighted by the weights to generate the output image volume. In a seventh example of the method optionally including one or more of the first through sixth examples, the method further comprises calculating the weights for blending the at least two input image volumes based on acquisition geometry. In an eighth example of the method optionally including one or more of the first through seventh examples, the at least two input image volumes are reconstructed from projection data acquired during a helical scan of a subject, and calculating the weights based on the acquisition geometry comprises calculating the weights based on a starting location for a table upon which the subject is positioned, a starting view angle for the helical scan, an ending view angle for the helical scan, and a helical pitch of the helical scan. In a ninth example of the method optionally including one or more of the first through eighth examples, the at least two input image volumes are reconstructed from projection data acquired during an axial scan of a subject, and wherein calculating the weights based on the acquisition geometry comprises calculating the weights based on a starting view angle of the axial scan and an ending view angle of the axial scan. In a tenth example of the method optionally including one or more of the first through ninth examples, calculating the weights based on the acquisition geometry further comprises calculating the weights based on an overlap region between the at least two input image volumes. In an eleventh example of the method optionally including one or more of the first through tenth examples, the method further comprises calculating noise-neutral blending weights for blending the at least two input image volumes, wherein adaptively blending the at least two input image volumes comprises blending the at least two input image volumes according to the noise-neutral blending weights to obtain at least two noise-adjusted image volumes, and blending the at least two noise-adjusted image volumes based on the weights to obtain the output image volume.

In another embodiment, a method comprises reconstructing a first image volume from a first set of projection data acquired during a scan of a subject, reconstructing a second image volume from a second set of projection data acquired during the scan, denoising the first image volume to generate a first denoised image volume, denoising the second image volume to generate a second denoised image volume, blending the first image volume and the first denoised image volume based on noise-neutral blending weights to generate a first noise-adjusted image volume, blending the second image volume and the second denoised image volume based on the noise-neutral blending weights to generate a second noise-adjusted image volume, and blending the first noise-adjusted image volume and the second noise-adjusted image volume based on locational blending weights to generate a noise-neutral blended image.

In a first example of the method, the method further comprises calculating the locational blending weights based on an overlap between the first image volume and the second image volume. In a second example of the method optionally including the first example, the method further comprises calculating the noise-neutral blending weights based on the locational blending weights, a prescribed blending ratio, and a tuning parameter related to noise levels in the first image volume and the first denoised image volume. In a third example of the method optionally including one or more of the first and second examples, denoising the first image volume and the second image volume comprises filtering the first image volume and the second image volume with non-linear image filters.

In yet another embodiment, a system comprises an x-ray source configured to generate a beam of x-rays towards a subject, a detector array comprising a plurality of detector elements configured to detect the beam of x-rays attenuated by the subject, and a computing device communicatively coupled to the x-ray source and the detector array, the computing device configured with instructions in non-transitory memory that when executed cause the computing device to adaptively blend at least two input image volumes, reconstructed from projection data acquired via the detector array, with different spatially-variant noise characteristics to generate an output image volume with uniform noise throughout the output image volume.

In a first example of the system, the computing device is further configured with instructions in the non-transitory memory that when executed cause the computing device to reconstruct a first image volume and a second image volume from the projection data, wherein image noise of the second image volume is reduced relative to image noise of the first image volume, and wherein the at least two input image volumes comprises the first image volume and the second image volume. In a second example of the system optionally including the first example, the computing device is further configured with instructions in the non-transitory memory that when executed cause the computing device to: reconstruct the first image volume via filtered backprojection, and process the second image volume with one or more noise-reduction methods to reduce the image noise of the second image volume. In a third example of the system optionally including one or more of the first and second examples, the computing device is further configured with instructions in the non-transitory memory that when executed cause the computing device to reconstruct the first image volume via filtered backprojection, and reconstruct the second image volume via one of an iterative reconstruction algorithm, a convolutional neural network trained to reconstruct the second image volume with reduced noise, or filtered backprojection with a different convolution kernel.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. Although the examples provided herein are related to medical application, the scope of the present disclosure covers non-destructive testing in industrial, biomedical, and other fields. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
reconstructing a first image volume from a first set of projection data acquired during a scan of a subject;
reconstructing a second image volume from a second set of projection data acquired during the scan;
denoising the first image volume to generate a first denoised image volume;
denoising the second image volume to generate a second denoised image volume;
blending the first image volume and the first denoised image volume based on noise-neutral blending weights to generate a first noise-adjusted image volume;
blending the second image volume and the second denoised image volume based on the noise-neutral blending weights to generate a second noise-adjusted image volume; and
blending the first noise-adjusted image volume and the second noise-adjusted image volume based on locational blending weights to generate a noise-neutral blended image.

2. The method of claim 1, further comprising calculating the locational blending weights based on an overlap between the first image volume and the second image volume.

3. The method of claim 1, further comprising calculating the noise-neutral blending weights based on the locational blending weights, a prescribed blending ratio, and a tuning parameter related to noise levels in the first image volume and the first denoised image volume.

4. The method of claim 1, wherein denoising the first image volume and the second image volume comprises filtering the first image volume and the second image volume with non-linear image filters.

5. A system, comprising:
an x-ray source configured to generate a beam of x-rays towards a subject;
a detector array comprising a plurality of detector elements configured to detect the beam of x-rays attenuated by the subject; and
a computing device communicatively coupled to the x-ray source and the detector array, the computing device configured with instructions in non-transitory memory that when executed cause the computing device to:
adaptively blend at least two noise-adjusted input image volumes, reconstructed from projection data acquired via the detector array, with different spatially-variant noise characteristics to generate an output image volume with uniform noise throughout the output image volume, wherein the each of the at least two noise-adjusted input image volumes includes an image volume and a corresponding denoised image volume blended based on the noise-neutral blending weights.

6. The system of claim 5, wherein the computing device is further configured with instructions in the non-transitory memory that when executed cause the computing device to: reconstruct a first image volume and a second image volume from the projection data, wherein image noise of the second image volume is reduced relative to image noise of the first image volume, and wherein the at least two noise-adjusted input image volumes comprises the first image volume and the second image volume.

7. The system of claim 6, wherein the computing device is further configured with instructions in the non-transitory memory that when executed cause the computing device to: reconstruct the first image volume via filtered backprojection, and process the second image volume with one or more noise-reduction methods to reduce the image noise of the second image volume.

8. The system of claim 5, wherein the computing device is further configured with instructions in the non-transitory memory that when executed cause the computing device to: reconstruct the first image volume via filtered backprojection, and reconstruct the second image volume via one of an iterative reconstruction algorithm, a convolutional neural network trained to reconstruct the second image volume with reduced noise, or filtered backprojection with a different convolution kernel.

* * * * *